United States Patent
Fredriksson et al.

(10) Patent No.: US 6,739,342 B1
(45) Date of Patent: May 25, 2004

(54) DEVICE FOR THERAPEUTIC PURPOSES ON HUMAN TISSUE, FOR INFLUENCING INJECTED MAGNETIC PARTICLES WITH AN ALTERNATING ELECTRO-MAGNETIC GRADIENT FIELD

(75) Inventors: Sarah Fredriksson, Staffanstorp (SE); Dario Kriz, Höör (SE)

(73) Assignee: European Institute of Science AB, Lund (SE)

( * ) Notice: Subject to any disclaimer, the term of this patent is extended or adjusted under 35 U.S.C. 154(b) by 141 days.

(21) Appl. No.: 10/049,506

(22) PCT Filed: Sep. 7, 2000

(86) PCT No.: PCT/SE00/01730

§ 371 (c)(1), (2), (4) Date: Feb. 13, 2002

(87) PCT Pub. No.: WO01/17611

PCT Pub. Date: Mar. 15, 2001

(30) Foreign Application Priority Data

Sep. 8, 1999 (SE) ................................................ 9903185

(51) Int. Cl.$^7$ .............................................. A61B 19/00
(52) U.S. Cl. ..................................................... 128/899
(58) Field of Search ................. 600/9–15; 128/897–899

(56) References Cited

U.S. PATENT DOCUMENTS

| | | |
|---|---|---|
| 4,303,636 A | 12/1981 | Gordon |
| 4,323,056 A | 4/1982 | Borrelli et al. |
| 4,662,359 A | 5/1987 | Gordon |
| 4,662,952 A | 5/1987 | Barringer et al. |
| 4,983,159 A | 1/1991 | Rand |
| 5,197,940 A * | 3/1993 | Sievert et al. .................. 600/9 |
| 5,429,583 A * | 7/1995 | Paulus et al. .................. 600/2 |
| 5,468,210 A * | 11/1995 | Matsui et al. .................. 600/10 |
| 5,643,246 A * | 7/1997 | Leeb et al. .............. 604/890.1 |

FOREIGN PATENT DOCUMENTS

| | | |
|---|---|---|
| JP | 11-57031 | 3/1999 |
| RU | 2080133 | 6/1998 |

OTHER PUBLICATIONS

"Magnetic Fluid Hyperthermia (MFH)", by A. Jordan et al. that appeared in *Scientific and Clinical Applications of Magnetic Carriers*, Plenum Press, New York, pp. 569 to 595 (1997).

\* cited by examiner

*Primary Examiner*—Samuel G. Gilbert
(74) *Attorney, Agent, or Firm*—Burns, Doane, Swecker & Mathis, L.L.P.

(57) ABSTRACT

A new device for therapeutic influence, change, decomposition of various biological structures in vivo or in vitro by means of an externally applied alternating magnetic gradient field is described.

24 Claims, 3 Drawing Sheets

FIG. 1A
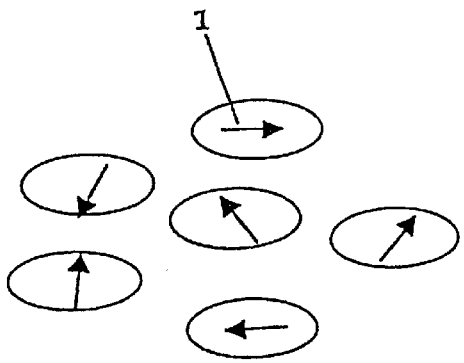
FIG. 1B
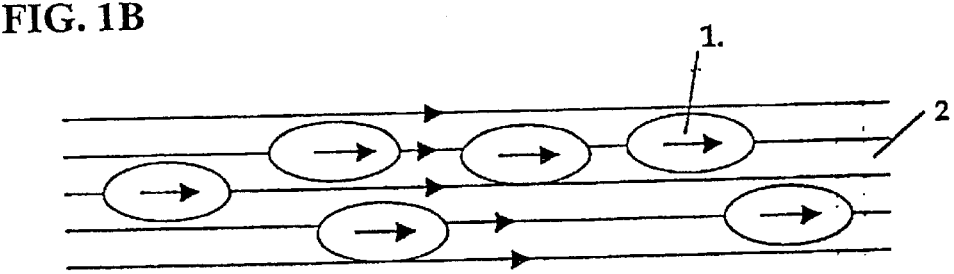
FIG. 1C
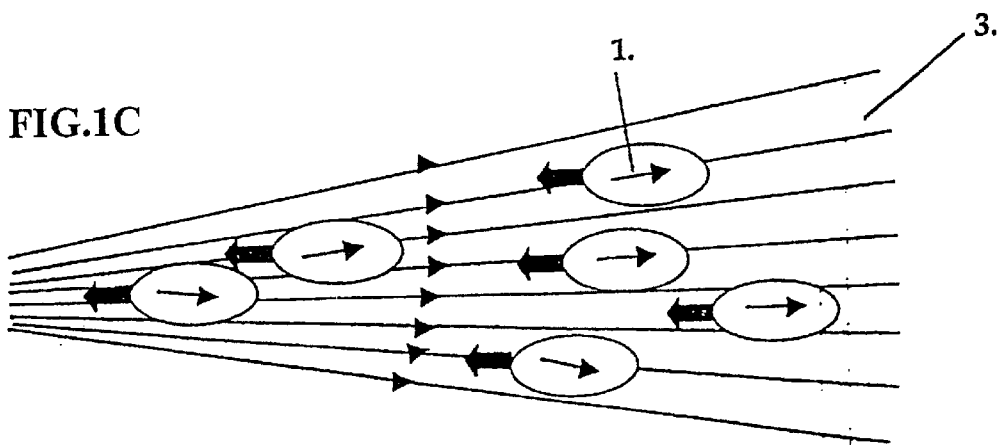
Fig 1

DEVICE FOR THERAPEUTIC PURPOSES ON HUMAN TISSUE, FOR INFLUENCING INJECTED MAGNETIC PARTICLES WITH AN ALTERNATING ELECTRO-MAGNETIC GRADIENT FIELD

The present invention relates to equipment for changing, weakening or destroying biological structures in vivo and in vitro by means of a magnetic gradient field.

BACKGROUND OF THE INVENTION

Magnetism and magnetically responsible particles have been used for a long time in various biochemical and medical applications. When paramagnetic materials are exposed to an externally alternating homogeneous magnetic field, heat is generated due to hysteresis. This generation of heat, in particular in combination with superparamagnetic nanoparticles, is used in cancer therapy and is then referred to as magnetic fluid hyperthermia (1). A cancer cell normally has a higher temperature than a healthy cell and therefore does not tolerate as high a temperature rise as a healthy cell. Thus, the cancer cells can be selectively destroyed or weakened without affecting the host organism. An alternative method is that the composition of the superparamagnetic particles is of such type that cancer cells are made to take in said particles into the cell, whereby the temperature is raised more efficiently in the cancer cell without any considerable heat loss to the environment. This type of therapy has been found to be promising, which is described, inter alia, in the patent literature (2, 3, 4, 5), even if there is no clinically approved magnetic equipment for this purpose for the time being.

A cell membrane is, inter alia, composed of lipids and fatty acids, which both have poor thermal conductivity, which makes it difficult to fight the target cell efficiently with only extracellular heat generated by hysteresis.

SUMMARY OF THE INVENTION

According to the present invention, a device is provided which solves the above-mentioned problems. Thus, a device is provided for increasing the thermal and/or kinetic energy of magnetically responsible particles, said device containing at least two magnetic field generating means, of which at least one is a coil, between which means an alternating magnetic gradient field can be generated in a spatially defined area, into which spatially defined area human or animal tissue can be introduced, said alternating magnetic gradient field causing an increase of the thermal and/or kinetic energy of magnetically responsible particles which have been added to said tissue, the increased thermal and/or kinetic energy of the magnetically responsible particles selectively reducing, deactivating or destroying endogenous or exogenous biological structures in said tissue.

In one embodiment of the invention, one of the magnetic field generating means is a permanent magnet.

In another embodiment of the invention, the device contains at least two coils and these coils are fed with alternating currents having different frequencies and/or amplitudes and/or phases, or alternatively said coils are fed with either the positive or the negative part of the fed alternating current.

Furthermore, the device can suitably be equipped with a thermostat for careful temperature control of said tissue and/or with variable time setting for careful control of the time during which said tissue is exposed to the alternating magnetic gradient field.

In one embodiment of the device, the alternating magnetic gradient field alternates with frequencies of up to 30 MHz and the field strength inside said coils amounts to at least 10 mT.

The tissue which is to be treated can be a body part or an inner organ or blood, which are returned to the host organism after completed exposure to the alternating magnetic gradient field.

The magnetically responsible particles suitably comprise a core of a metal oxide and a coating containing antibodies or parts thereof and have a size of 0.1–300 nm.

The magnetically responsible particles have been added to the host organism before the exposure of its tissue to the alternating magnetic gradient field, or alternatively after the tissue has been temporarily removed from the host organism.

The endogenous or exogenous biological structures consist, for instance, of mammal cells, malignant cells, plant cells, nerve cells, bacteria, viruses, cellular organelles, cell membranes, cell walls, liposomes, proteins, protozoa, parasites, peptides, drugs, toxins, organic compounds, inorganic compounds, or combinations thereof.

According to one aspect, the device is intended for in vivo or in vitro treatment of tumour diseases, endocrine disorders or infectious diseases.

BRIEF DESCRIPTION OF THE DRAWINGS

FIG. 1 is a schematic illustration of the behaviour of magnetically responsible materials in one embodiment of the device according to the invention.

DETAILED DESCRIPTION OF THE INVENTION

By the present invention, a new device is provided for use in a completely new method which combines the generation of heat by hysteresis with a powerful introduction of shearing forces. The shearing forces initiate dislocations in the biological structure, for instance in cell membranes, cell walls (in cases where the target cell is e.g. a bacterium) or in intracellular components due to mechanical fatigue, which causes damage in the structures. The method is based on the use of an externally applied gradient magnetic field.

Below, the invention will be described in more detail by means of the drawings, which show embodiments of the invention.

FIG. 1 illustrates how a magnetically responsible particle is affected by a magnetic gradient field. Without the action of an external magnetic field, the dipoles 1 in the magnetically responsible particles are randomly oriented (FIG. 1A). When the particles are exposed to a homogeneous magnetic field 2, the dipoles are oriented according to the direction of the field (FIG. 1B). When the direction of the homogeneous field alternates, the dipoles will alternate according to the field direction of the external homogeneous field. When the applied magnetic field is non-homogeneous, i.e. is a gradient magnetic field 3, the dipoles in the magnetically responsible particles will be aligned with the field direction at the same time as the magnetically responsible particles will move towards the gradient according to FIG. 1C.

Furthermore, by alternating the direction of the gradient, the magnetically responsible particle can be brought into mechanical vibration (due to the influence of forces it will alternately change directions).

Moreover, a combination of said magnetic gradient field with a homogeneous magnetic field can be provided either simultaneously or with a time shift so that a better orientation of the dipoles and greater shearing forces can be obtained.

Figure 2:
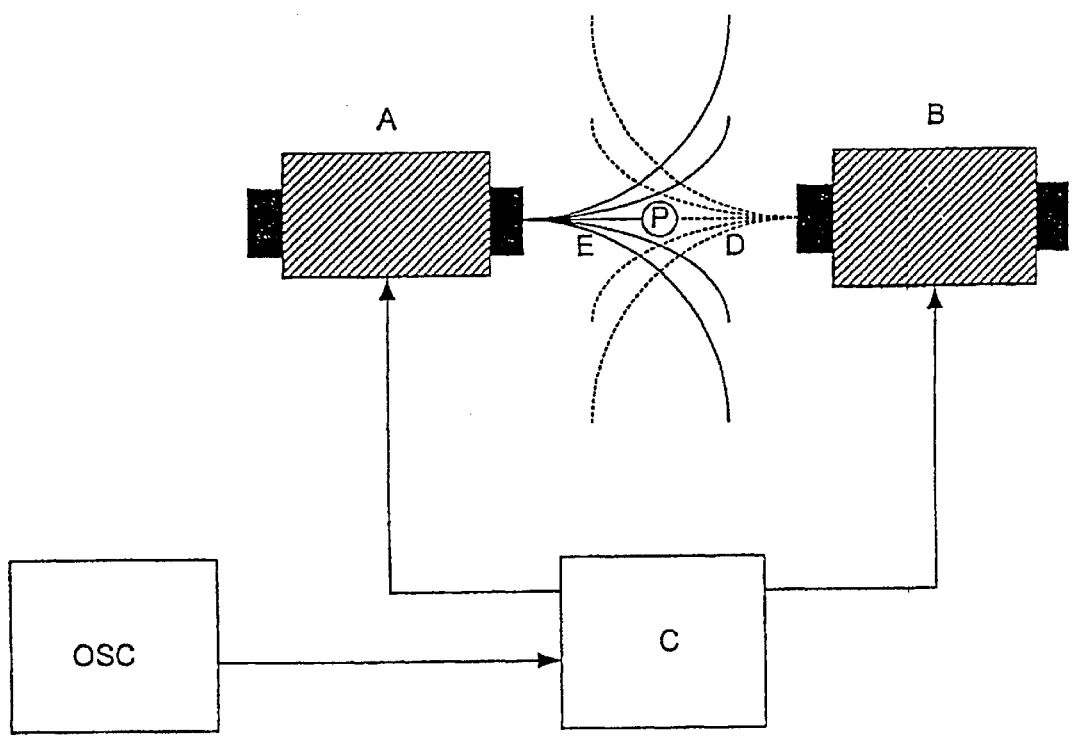
FIG. 2 is a schematic illustration of the structure of one embodiment of the device according to the invention for generating a magnetic gradient field with alternating gradient direction.

The generation of a gradient magnetic field whose direction periodically alternates (periodically shifts) requires a device according to the invention, for instance, as illustrated in FIG. 2. The functional principle is based on two coils A and B (with or without a ferrite core) being placed opposite to each other. A control unit C controls the current through the coils so that only one of the coils at a time has a current flowing through its windings. This alternation of current, whose frequency is controlled by the oscillator (OSC), causes the coils to alternately create the gradient magnetic fields D and E with different gradient directions. A biological structure or a magnetically responsible particle P located between the coils will be exposed to a gradient magnetic field with periodically alternating direction, which will induce a mechanical vibration according to the description above.

The present invention also comprises variants, in which, for instance, the current intensity or its direction through the windings of the coils can be controlled so that more efficient vibrations can be obtained. A very useful special case is to let the gradient direction alternate but maintain the orientation of the dipoles by always letting the field direction be the same. This results in advantages, such as no provision of hysteresis (no generation of heat), while the vibration frequency (=kinetic energy) can be increased since the alternation rate of the dipoles will not be limited by the tendency of the magnetic material to counteract the alternation of the dipole directions.

It is also possible to introduce additional coils to obtain more efficient or more directional vibrations.

Figure 3:
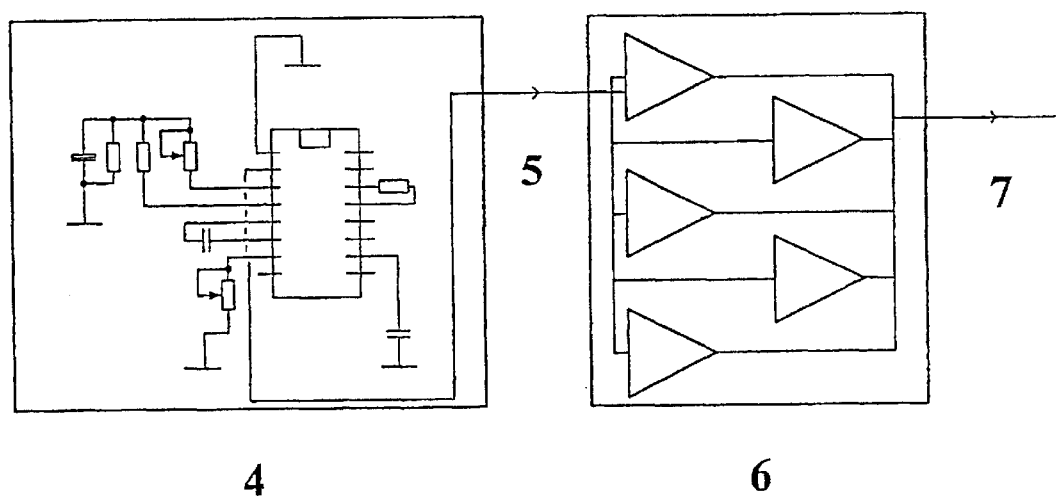
FIG. 3 is an illustration of an electronic circuit which can be used to feed the coils in one embodiment of the device according to the invention with alternating current.

FIG. 3 illustrates an example of an electronic circuit which can be used to feed the coils in the device according to the invention with alternating current. The circuit contains an oscillator 4 based on the circuit XR2206, whose output signal 5 is amplified by a power amplifying step 6, which is connected in parallel and based on 5 circuits of the type PBD 3548/1 (manufactured by Ericsson), whose output signal 7 can drive an alternating current (maximum 1 MHz, 10 A) through one or more coils.

It is obvious to the one skilled in the art that the above-described electronic circuit in FIG. 3 is easy to modify and that the same result can be obtained by means of various alternative prior-art connections of oscillators and power amplifiers.

One example of the connection of the coils is that each coil constitutes a part of an oscillation circuit consisting of a 0.5 Ω resistor, a 127 pF capacitor and a 200 µH coil, which are connected in series, which oscillation circuit is fed with alternating current such as shown in FIG. 3.

An alternating gradient field is obtained between two coils which are part of said oscillation circuit and applied to an electronic circuit each, as shown in FIG. 3, with the difference, however, that the coils are fed with 1.0 MHz and 0.9 MHz, respectively. The variation of the gradient field will be dependent on the difference frequency 1.0 MHz–0.9 MHz.

It is obvious to the one skilled in the art that the above-described example is easy to modify and that the same result can be achieved by means of various alternative connections and coils.

REFERENCES

1. Jordan A., Wust P., Scholz R., Faehling H., Krause J. & Felix R. Magnet Fluid Hyperthermia, 569–597, in Scientific and Clinical Applications of Magnetic Carriers, edited by Häfeli U., Schutt W,. Teller J. and Zborowski M. Plenum Press 1997.
2. Gordon R. T. Cancer treatment. U.S. Pat. No. 4,303,636, 1981.
3. Gordon R. T. Cancer treatment method. U.S. Pat. No. 4,662,952, 1986.
4. Gordon R. T. Use of magnetic susceptibility probes in the treatment of cancer. U.S. Pat. No. 4,662,359, 1987.
5. Borelli N. F., Luderer A. A. & Panzarino J. N. Radio frequency induced hyperthermia for tumor therapy. U.S. Pat. No. 4,323,056, 1982.

We claim:

1. A device for increasing the thermal and/or kinetic energy of magnetically responsible particles, wherein the device contains at least two magnetic field generating means, of which at least one is a coil, between which means an alternating magnetic gradient field can be generated in a spatially defined area, into which spatially defined area human or animal tissue can be introduced, said alternating magnetic gradient field causing an increase of the thermal and/or kinetic energy of magnetically responsible particles which have been added to said tissue, the increased thermal and/or kinetic energy of the magnetically responsible particles selectively reducing, deactivating or destroying endogenous or exogenous biological structures in said tissue.

2. A device as claimed in claim 1, wherein one of the magnetic field generating means is a permanent magnet.

3. A device as claimed in claim 2, wherein the device contains at least two coils, and these coils are fed with alternating currents having at least one of different frequencies and different amplitudes and different phases.

4. A device a claimed in claim 3, wherein the device is equipped with at least one of a thermostat for careful temperature control of said tissue, and a variable time setting for careful control of the time during which said tissue is exposed to the alternating magnetic gradient field.

5. A device a claimed in claim 2, wherein the device is equipped with at least one of a thermostat for careful temperature control of said tissue, and a variable time setting for careful control of the time during which said tissue is exposed to the alternating magnetic gradient field.

6. A device as claimed in claim 2, wherein the alternating magnetic gradient field alternates with frequencies of up to 30 Mhz, and the field strength inside said coils amounts to at least 10 mT.

7. A device as claimed in claim 2, wherein said spatially defined area is adapted to receive human or animal tissue, and
   said tissue consists of a body part or an inner organ or blood, which are returned to the host organism after completed exposure to the alternating magnetic gradient field.

8. A device as claimed in claim 2, wherein said magnetically responsible particles comprise a core of a metal oxide and a coating containing antibodies or parts thereof and have a size of 1–300 nm.

9. A device as claimed in claim 2, further including magnetically responsible particles, wherein
   said magnetically responsible particles have been at least one of added to the host organism before the exposure of its tissue to the alternating magnetic gradient field, or added to the tissue after the tissue has been temporarily removed from the host organism.

10. A device as claimed in claim 2, further including endogenous or exogenous biological structures, wherein said endogenous or exogenous biological structures consist of mammal cells, malignant cells, plant cells, nerve cells, bacteria, viruses, cellular organelles, cell membranes, cell walls, liposomes, proteins, protozoa, parasites, peptides, drugs, toxins, organic compounds, inorganic compounds, or combinations thereof.

11. A device as claimed in claim 2, wherein the device contains at least two coils, and each of said coils is fed with one of the positive or the negative part of an alternating current.

12. A device as claimed in claim 11, wherein the device is equipped with at least one of a thermostat for careful temperature control of said tissue, and a variable time setting for careful control of the time during which said tissue is exposed to the alternating magnetic gradient field.

13. A device as claimed in claim 1, wherein the device contains at least two coils, and these coils are fed with alternating currents having at least one of different frequencies and different amplitudes and different phases.

14. A device as claimed in claim 13, wherein the device is equipped with at least one of a thermostat for careful temperature control of said tissue, and a variable time setting for careful control of the time during which said tissue is exposed to the alternating magnetic gradient field.

15. A device as claimed in claim 1, wherein the device is equipped with at least one of a thermostat for careful temperature control of said tissue, and a variable time setting for careful control of the time during which said tissue is exposed to the alternating magnetic gradient field.

16. A device as claimed in claim 1, wherein said spatially defined area is adapted to receive human or animal tissue, and said tissue consists of a body part or an inner organ or blood, which are returned to the host organism after completed exposure to the alternating magnetic gradient field.

17. A device as claimed as in claim 1, further including magnetically responsible particles, wherein said magnetically responsible particles have been at least one of added to the host organism before the exposure of its tissue to the alternating magnetic gradient field, or added to the tissue after the tissue has been temporarily removed from the host organism.

18. A device as claimed in claim 1, further including endogenous or exogenous biological structures, wherein
said endogenous or exogenous biological structures consist of mammal cells, malignant cells, plant cells, nerve cells, bacteria, viruses, cellular organelles, cell membranes, cell walls, liposomes, proteins, protozoa, parasites, peptides, drugs, toxins, organic compounds, inorganic compounds, or combinations thereof.

19. A device as claimed in claim 1, wherein the device contains at least two coils, and each of said coils is fed with one of the positive or the negative part of an alternating current.

20. A device as claimed in claim 19, wherein the device is equipped with at least one of a thermostat for careful temperature control of said tissue, and a variable time setting for careful control of the time during which said tissue is exposed to the alternating magnetic gradient field.

21. A device for increasing the thermal and/or kinetic energy of magnetically responsible particles, wherein the device contains at least two magnetic field generating means, of which at least one is a coil, between which means an alternating magnetic gradient field can be generated in a spatially defined area, into which spatially defined are human or animal tissue can be introduced, said alternating magnetic gradient field causing an increase of the thermal and/or kinetic energy of magnetically responsible particles which have been added to said tissue, the increased thermal and/or kinetic energy of the magnetically responsible particles selectively reducing, deactivating or destroying endogenous or exogenous biological structures in said tissue, wherein
the alternating magnetic gradient field alternates with frequencies of up to 30 Mhz, and the field strength inside said coils amounts to at least 10 mT.

22. A device for increasing the thermal and/or kinetic energy of magnetically responsible particles, wherein the device contains at least two magnetic field generating means, of which at least one is a coil, between which means an alternating magnetic gradient field can be generated in a spatially defined area, into which spatially defined area human or animal tissue can be introduced, said alternating magnetic gradient field causing an increase of the thermal and/or kinetic energy of magnetically responsible particles which have been added to said tissue, the increased thermal and/or kinetic energy of the magnetically responsible particles selectively reducing, deactivating or destroying endogenous or exogenous biological structures in said tissue, wherein
said magnetically responsible particles comprise a core of a metal oxide and a coating containing antibodies or parts thereof and have a size of 1–300 nm.

23. A method of using the device according to claim 1 for in vivo or in vitro use for treating tumour diseases, endocrine disorders or infectious diseases.

24. A method of using the device according to claim 2 for in vivo or in vitro use for treating tumour diseases, endocrine disorders or infectious diseases.

* * * * *